United States Patent
Enquist

(10) Patent No.: US 7,622,080 B2
(45) Date of Patent: Nov. 24, 2009

(54) HYDROGEN GAS SENSITIVE SEMICONDUCTOR SENSOR

(75) Inventor: Fredrik Enquist, Linköping (SE)

(73) Assignee: Adixen Sensistor AB, Linköping (SE)

( * ) Notice: Subject to any disclaimer, the term of this patent is extended or adjusted under 35 U.S.C. 154(b) by 97 days.

(21) Appl. No.: 11/524,332

(22) Filed: Sep. 21, 2006

(65) Prior Publication Data
US 2007/0069313 A1    Mar. 29, 2007

Related U.S. Application Data

(60) Provisional application No. 60/718,730, filed on Sep. 21, 2005.

(30) Foreign Application Priority Data
Sep. 21, 2005    (SE) ................... 0502088

(51) Int. Cl.
*H01L 257/414* (2006.01)
(52) U.S. Cl. ............ 422/88; 422/83; 422/50; 257/414; 257/471; 257/472
(58) Field of Classification Search .............. 422/88; 73/31.06; 374/178; 204/406
See application file for complete search history.

(56) References Cited

U.S. PATENT DOCUMENTS

| | | | | |
|---|---|---|---|---|
| 3,975,253 A | * | 8/1976 | Radd et al. | 204/406 |
| 4,058,368 A | * | 11/1977 | Svensson et al. | 422/88 |
| 4,795,968 A | | 1/1989 | Madou et al. | |
| 6,041,643 A | * | 3/2000 | Stokes et al. | 73/31.06 |
| 6,109,094 A | * | 8/2000 | Baranzahi et al. | 73/31.06 |
| 6,484,563 B1 | | 11/2002 | Enquist et al. | |
| 6,569,779 B1 | | 5/2003 | Lundstrom et al. | |

FOREIGN PATENT DOCUMENTS

| | | |
|---|---|---|
| DE | 3151891 A1 | 7/1983 |
| DE | 36 34 132 A1 | 4/1987 |
| GB | 2 183 344 A | 6/1987 |

(Continued)

OTHER PUBLICATIONS

European Patent Search Report, dated Apr. 17, 2007, issued for corresponding European Application No. EP 06 12 0254.

(Continued)

*Primary Examiner*—Walter D Griffin
*Assistant Examiner*—Christine T Mui
(74) *Attorney, Agent, or Firm*—Venable LLP; Eric J. Franklin

(57) ABSTRACT

A hydrogen gas sensitive semiconductor sensor including a catalytic metal layer, a semiconductor layer and an insulator layer arranged between the catalytic metal layer and the semiconductor layer. The catalytic metal layer includes an outer surface and an inner surface including at least one hydrogen atom adsorption surface portion. Each hydrogen atom adsorption surface portion is arranged adjacent to the insulator layer. The surface area of the outer surface is at least 100% larger than the total surface area of all of the at least one hydrogen atom adsorption surface portion. A probe includes the sensor, A hydrogen gas detection system includes the sensor. Use of the sensor for detection of presence of and/or measurement of concentration of hydrogen gas in a gas sample.

20 Claims, 3 Drawing Sheets

FOREIGN PATENT DOCUMENTS

| | | |
|---|---|---|
| SE | 387 444 | 9/1974 |
| WO | WO 01/69228 A2 | 9/2001 |
| WO | WO 03/002999 * | 1/2003 |

OTHER PUBLICATIONS

K. Tajima et al., "RF-Sputtered SiGe Thin Film for Thermoelectric Hydrogen Sensor," Abs. 1460, 204$^{th}$ Meeting, © *2003 The Electrochemical Society, Inc.*

Ingemar Lundstrom, "Hydrogen Sensitive MOS-Structures Part 1. Principles and Applications," *Sensors and Acturators*, 1, pp. 403-426 (1981).

U. Ackelid et al.; Metal-Oxide-Semiconductor Structures with Thermally Activitated Sensitivity to Ethanol Vapour and Unsaturated Hydrocarbons; Proc. of the 2nd int. meeting on chemical sensors; 1986; pp. 395-398.

Mikael Löfdahl et al.; Gas response dependence on gate metal morphology of field-effect devices; Sensors and Actuators B 80; 2001; pp. 183-192.

* cited by examiner

HYDROGEN GAS SENSITIVE SEMICONDUCTOR SENSOR

This application claims priority to Swedish patent application 0502088-8 filed 21 Sep. 2005 and U.S. provisional patent application 60/718,730 filed 21 Sep. 2005.

FIELD OF THE INVENTION

The present invention relates to a hydrogen gas sensitive semiconductor sensor. Furthermore, the present invention relates to the use of the hydrogen gas sensitive semiconductor sensor according to the invention for detection of presence of hydrogen gas molecules in a gas sample as well as the use of the hydrogen gas sensitive semiconductor sensor according to the invention for measurement of the concentration of hydrogen gas molecules in a gas sample. In addition, the present invention relates to a probe comprising the hydrogen gas sensitive semiconductor sensor according to the invention and a hydrogen gas detection system comprising the hydrogen gas sensitive semiconductor sensor according to the invention.

BACKGROUND OF THE INVENTION

Detection of specific gaseous atoms or molecules in a gas sample may today be performed using any of a large number of different devices, ranging from complex technical systems like, for example, mass spectrometers and gas chromatographs, to small and relatively simple sensors like, for example, sensors measuring the thermal conductivity of a gas. Most of these devices are based on measurement of a physical or chemical property of gaseous atoms or molecules, whereas some of them instead are based on measurement of the actual presence of specific gaseous atoms or molecules.

For example, one device that may be used for detection of specific gaseous molecules in a gas sample and that is based on measurement of the actual presence of specific gaseous molecules, is described in SE 387444. More specifically, SE 387444 describes a gas sensitive sensor that may be used for detection of hydrogen gas.

There are many different applications in which devices for detection of hydrogen gas are necessary, useful or desired to utilize. For example, such a device may be utilized as a leak detector in systems using hydrogen gas, as a leak detector in systems and methods using hydrogen gas as a tracer gas for testing and/or locating leaks, or as an alarm detector to indicate the presence of hydrogen gas within, for example, industries using hydrogen gas or gas mixtures containing hydrogen gas (such as petrochemical industries, electrochemical industries, gasworks) for the purpose of preventing explosions.

The gas sensitive sensor described in SE 387444 comprises a catalytic metal layer constituting a metal electrode, a semiconductor layer and an insulator layer arranged between the catalytic metal layer and the semiconductor layer. Since this sensor comprises a semiconductor structure, it is herein denoted as a gas sensitive semiconductor sensor. The catalytic metal layer is made of any of the platinum metals palladium, nickel and platinum or an alloy containing at least 20% palladium by atomic weight.

The working principle of the semiconductor sensor in SE 387444 for detection of hydrogen gas is based on the fact that some of the platinum metals, especially palladium, are able to adsorb hydrogen gas molecules and dissociate adsorbed hydrogen gas molecules on their surfaces, to dissolve and allow penetration of hydrogen atoms thus formed and to adsorb hydrogen atoms at their surfaces. The term "catalytic metal" is herein used to denote a metal or an alloy being capable to dissociate hydrogen gas molecules and to absorb the hydrogen atoms thus formed.

The basic working principle of the semiconductor sensor in SE 387444 will now be described for the case when the sensor is utilized for detection of hydrogen gas. When the semiconductor sensor in SE 387444 is exposed to hydrogen gas molecules, the catalytic metal layer may adsorb some of them on its outer surface arranged to freely communicate with the ambient atmosphere. The adsorbed hydrogen gas molecules may then be dissociated on the outer surface and the hydrogen atoms thus formed may be absorbed into the catalytic metal layer. Some of the absorbed hydrogen atoms will subsequently be adsorbed at the interface between the catalytic metal layer and the insulator layer after diffusion through the catalytic metal layer.

Furthermore, it is well established that hydrogen atoms adsorbed at the interface between the catalytic metal layer and the insulator layer are polarized with the positive end facing the insulator layer (Lundström, I., Sensors and Actuators 1, 403 (1981)). The polarization implies that hydrogen dipoles are produced. The hydrogen dipoles generate an electrical field that shifts the effective work function of the catalytic metal layer. In consequence of the shift of the effective work function of the catalytic metal layer, the electrical function of the semiconductor sensor is influenced, i.e. a voltage shift in the characteristics of the semiconductor sensor is generated, and this influence is utilized for the detection of hydrogen gas. This sensing principle is herein referred to as the "hydrogen dipole transducer principle".

The shift of the effective work function of the catalytic metal layer generated by hydrogen atoms adsorbed at the interface between the catalytic metal layer and the insulator layer may not only be utilized for detection of presence of hydrogen gas in a gas sample, but also for measurement of the concentration of hydrogen gas in a gas sample. The magnitude of the shift is determined by the number of hydrogen atoms adsorbed per unit area, i.e. the density of hydrogen atoms, at the interface between the catalytic metal layer and the insulator layer. Since the amount of hydrogen gas molecules in a gas sample and the amount of hydrogen atoms adsorbed at the interface between the catalytic metal layer and the insulator layer equilibrate after a certain time, the magnitude of the equilibrium shift may be utilized as a measure of the concentration of hydrogen gas molecules in a gas sample. However, the time before equilibrium is achieved between the amount of hydrogen gas molecules in a gas sample and the amount of hydrogen atoms adsorbed at the interface between the catalytic metal layer and the insulator layer is usually relatively long. For that reason, it is preferred to utilize the rate with which the effective work function is shifted, i.e. the rate with which the output signal is shifted, before an equilibrium shift is achieved, as a measure of the concentration of hydrogen gas molecules in a gas sample. Furthermore, the magnitude of the shifting rate of the effective work function and the magnitude of the equilibrium shift at a certain concentration of hydrogen gas molecules in a gas sample are of course dependent on the sensitivity to hydrogen gas molecules of the sensor.

A hydrogen gas sensitive semiconductor sensor working based on the same working principle as the sensor in SE 387444, i.e. based on the so-called hydrogen dipole transducer principle, is hereinafter denoted as a "hydrogen gas sensitive semiconductor sensor working based on the hydrogen dipole transducer principle".

Hydrogen gas sensitive semiconductor sensors working based on the hydrogen dipole transducer principle are known to have a very high selectivity for hydrogen gas when operated up to around 150° C. However, it has been shown that such sensors have high sensitivities also to other gaseous hydrogen-containing molecules, such as alcohols and unsaturated hydrocarbons, when operated at higher temperatures. For example, sensitivity to methanol and ethanol of sensors working based on the hydrogen dipole transducer principle have been shown when operated at temperatures above 150° C. (Ackelid, U. et al, Metal-Oxide-Semiconductor structures with thermally activated sensitivity to ethanol vapour and unsaturated hydrocarbons, Proc. $2^{nd}$ Int. Meet., Chemical Sensors, Bordeaux 1986, pp 395-398). In the same way as hydrogen gas molecules, such gaseous hydrogen-containing molecules are then adsorbed and dissociated on the outer surface of the catalytic metal layer and hydrogen atoms thus formed are absorbed into the catalytic metal layer.

Thus, semiconductor sensors working based on the hydrogen dipole transducer principle may not only be utilized for detection of hydrogen gas molecules, but also for detection of other gaseous hydrogen-containing molecules. However, when such sensors are to be utilized for detection of hydrogen gas, they are preferably operated at temperatures below 150° C. in order to obtain as high selectivity for hydrogen gas as possible and to avoid sensitivity to other gaseous hydrogen-containing molecules to which the sensor is sensitive when operated at higher temperatures.

The characteristic sensitivity to hydrogen gas molecules of a specific hydrogen gas sensitive semiconductor sensor working based on the hydrogen dipole transducer principle depends on the catalytic property of the catalytic metal layer, i.e. the ability of the catalytic metal layer to dissociate hydrogen gas molecules on the outer surface and to absorb hydrogen atoms thus formed. The reason for why the catalytic property of the catalytic metal layer influences the sensitivity is of course that it influences the number of hydrogen atoms that may be adsorbed per unit area, i.e. the density of hydrogen dipoles, at the interface between the catalytic metal layer and the insulator layer at a certain concentration of hydrogen gas in a gas sample.

However, the sensitivity of a hydrogen gas sensitive semiconductor sensor working based on the hydrogen dipole transducer principle may be reduced by, for example, oxidization of the outer surface of the catalytic metal layer. Oxygen in the surroundings of the semiconductor sensor may adsorb on, or bond to, the outer surface of the catalytic metal layer. Thereby, the number of adsorption sites, to which hydrogen gas molecules may adsorb, on the outer surface of the catalytic metal layer is being reduced concurrently with the number of molecules and atoms of oxygen being increased on the outer surface of the catalytic metal layer. When the number of adsorption sites, to which hydrogen gas molecules may adsorb, is reduced, the number of hydrogen gas molecules that may be adsorbed and dissociated on the outer surface of the catalytic metal layer and the number of hydrogen atoms that may be absorbed into the catalytic metal layer, at a certain concentration of hydrogen gas in a gas sample, are reduced. Thereby, the number of hydrogen atoms that may be adsorbed per unit area at the interface between the catalytic metal layer and the insulator layer, i.e. the number of hydrogen dipoles that may be achieved, at a certain concentration of hydrogen gas in a gas sample, is reduced. This implies that the sensitivity then is reduced.

Most gas samples subject to analysis regarding hydrogen gas contain air or oxygen gas. Thereby, the above mentioned reduction of the sensitivity of a hydrogen gas sensitive semiconductor sensor working based on the hydrogen dipole transducer principle is of frequent occurrence.

Furthermore, there are also other contaminants that may adsorb on, or bond to, the outer surface of the catalytic metal layer and thereby influence the sensitivity in the same way as oxygen. One example of such a contaminant is carbon monoxide, which also is present in many gas samples. In addition, hydrogen sulphide may bond to the outer surface of the catalytic metal layer.

When a hydrogen gas sensitive semiconductor sensor working based on the hydrogen dipole transducer principle is utilized under such detection conditions that oxygen and/or other contaminants may adsorb on, or bond to, the outer surface, the sensitivity of the sensor typically decays with sensor age due to oxidization or contamination by other contaminants of the outer surface. Usually, the life of a hydrogen gas sensitive semiconductor sensor working based on the hydrogen dipole transducer principle is substantially reduced under such detection conditions.

One way of counteracting the sensitivity reduction by oxygen and other contaminants is to purify the gas samples to be tested by the sensor from oxygen and other contaminating substances. Thereby, any influences on the sensitivity by oxygen and other contaminants are substantially counteracted and the life of the sensor is increased. However, such purification is relatively difficult and complicated to perform and results in that the total analysis time is lengthened since an extra step of sample preparation then is added to the analysis procedure.

Another way of counteracting the sensitivity reduction by oxygen and other contaminants is described in U.S. Pat. No. 6,484,563. According to the method described in U.S. Pat. No. 6,484,563, the semiconductor sensor is exposed to a gas sample during a detection interval. Each detection interval is preceded by a time interval during which the semiconductor sensor is kept in a surrounding preconditioning gas atmosphere containing negligible amounts of oxygen, hydrogen and carbon monoxide. The preconditioning time interval is much longer than the detection interval. The result during a preconditioning time interval is that essentially all oxygen and carbon monoxide, if any, adsorbed on the outer surface of the catalytic metal layer during a preceding detection interval are removed. Thereby, the above mentioned influences on the sensitivity by oxygen and other contaminants are substantially counteracted and the life of the sensor is increased. However, this method requires the use of equipment for modification of the atmosphere surrounding the semiconductor sensor.

The two above mentioned ways of counteracting the sensitivity reduction by oxygen and other contaminants may thus be utilized for increasing the life of a hydrogen gas sensitive semiconductor sensor working based on the hydrogen dipole transducer principle. However, these two ways do not increase the initial sensitivity of such a sensor. It is for most applications preferred, or required, that not only the life of a hydrogen gas sensitive semiconductor sensor working based on the hydrogen dipole transducer principle is as long as possible, but also that the initial sensitivity is as high as possible. The term "initial sensitivity" refers herein to the sensitivity of a sensor during an initial time period during an initial use of the sensor, i.e. the sensitivity of a "new" and not previously used sensor.

An increased initial sensitivity as well as an increased life of a hydrogen gas sensitive semiconductor sensor working based on the hydrogen dipole transducer principle may of course be achieved by modifying the catalytic property of the catalytic metal layer. One way to modify the catalytic property of the catalytic metal layer of a hydrogen gas sensitive semiconductor sensor working based on the hydrogen dipole principle in order to increase the initial sensitivity as well as the life is to utilize another catalytic metal assigning a higher initial sensitivity to the sensor. However, in most such sensors the catalytic metal known to assign the highest initial sensitivity to a hydrogen gas sensitive semiconductor sensor is already used today. Another way to modify the catalytic property of the catalytic metal layer of a hydrogen gas sensitive semiconductor sensor working based on the hydrogen dipole transducer principle in order to increase the initial sensitivity as well as the life is to increase the temperature of the outer surface during hydrogen gas detection. It is known that when the temperature is increased to above 150° C., the sensitivity to hydrogen gas is increased. However, the selectivity for hydrogen gas is reduced when the temperature is increased to above 150° C. and the sensitivity to other gaseous hydrogen-containing molecules, such as those mentioned above, is then increased.

There is still a need for a reliable way of increasing the initial sensitivity to hydrogen gas molecules as well as the life of a hydrogen gas sensitive semiconductor sensor working based on the hydrogen dipole transducer principle.

SUMMARY OF THE INVENTION

It is an object of the present invention to provide a hydrogen gas sensitive semiconductor sensor with increased initial sensitivity to hydrogen gas molecules as well as increased life, which sensor comprises a catalytic metal layer, a semiconductor layer and an insulator layer arranged between the catalytic metal layer and the semiconductor layer, whereby the catalytic metal layer comprises an outer surface and an inner surface, whereby the outer surface is arranged to freely communicate with the ambient atmosphere.

Thanks to that the inner surface comprises at least one hydrogen atom adsorption surface portion, whereby each hydrogen atom adsorption surface portion is arranged adjacent to the insulator layer, and that the surface area of the outer surface is at least 100% larger than the total surface area of all of the at least one hydrogen atom adsorption surface portion of the inner surface, it is possible to achieve a hydrogen gas sensitive semiconductor sensor with increased initial sensitivity to hydrogen gas molecules as well as increased life.

A further object of the present invention is to provide a probe for detection of hydrogen gas comprising a hydrogen gas sensitive semiconductor sensor with increased initial sensitivity to hydrogen gas molecules as well as increased life, which sensor comprises a catalytic metal layer, a semiconductor layer and an insulator layer arranged between the catalytic metal layer and the semiconductor layer, whereby the catalytic metal layer comprises an outer surface and an inner surface, whereby the outer surface is arranged to freely communicate with the ambient atmosphere.

Thanks to that the probe comprises a hydrogen gas sensitive semiconductor sensor in which the inner surface comprises at least one hydrogen atom adsorption surface portion, whereby each hydrogen atom adsorption surface portion is arranged adjacent to the insulator layer, and in which the surface area of the outer surface is at least 100% larger than the total surface area of all of the at least one hydrogen atom adsorption surface portion of the inner surface, it is possible to achieve a probe comprising a hydrogen gas sensitive semiconductor sensor with increased initial sensitivity to hydrogen gas molecules as well as increased life.

Another object of the present invention is to provide a hydrogen gas detection system comprising a probe and a measuring unit, which probe comprises a hydrogen gas sensitive semiconductor sensor with increased initial sensitivity to hydrogen gas molecules as well as increased life, which sensor comprises a catalytic metal layer, a semiconductor layer and an insulator layer arranged between the catalytic metal layer and the semiconductor layer, whereby the catalytic metal layer comprises an outer surface and an inner surface, whereby the outer surface is arranged to freely communicate with the ambient atmosphere.

Thanks to that the hydrogen gas detection system comprises a probe comprising a hydrogen gas sensitive semiconductor sensor in which the inner surface comprises at least one hydrogen atom adsorption surface portion, whereby each hydrogen atom adsorption surface portion is arranged adjacent to the insulator layer, and in which the surface area of the outer surface is at least 100% larger than the total surface area of all of the at least one hydrogen atom adsorption surface portion of the inner surface, it is possible to achieve a hydrogen gas detection system comprising a probe and a measuring unit, which probe comprises a hydrogen gas sensitive semiconductor sensor with increased initial sensitivity to hydrogen gas molecules as well as increased life.

Still other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures described herein.

BRIEF DESCRIPTION OF THE DRAWINGS

In the drawings, wherein like reference characters denote similar elements throughout the several views.

DETAILED DESCRIPTION OF THE INVENTION

Figure 1:
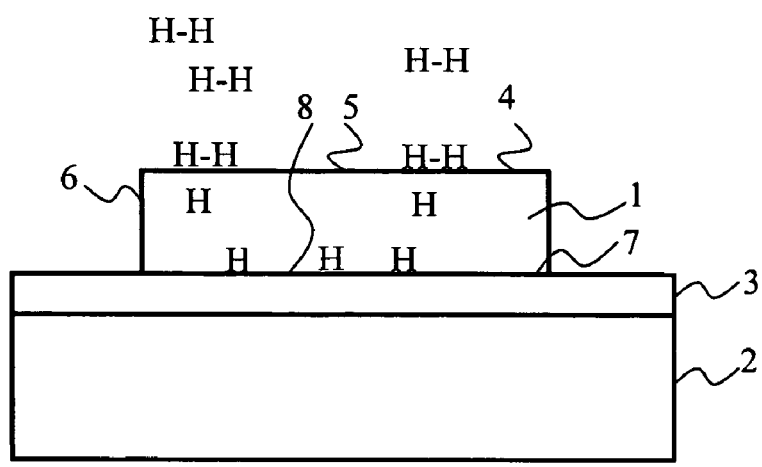
FIG. 1 is a schematic cross-sectional view of the basic structure and basic working principle of a prior art gas sensitive semiconductor sensor, which works based on the hydrogen dipole transducer principle and which may be utilized for detection of hydrogen gas.

FIG. 1 is a schematic cross-sectional view of the basic structure and basic working principle of a prior art gas sensitive semiconductor sensor, which works based on the hydrogen dipole transducer principle and which may be utilized for detection of hydrogen gas. Most prior art hydrogen gas sensitive semiconductor sensors working based on the hydrogen dipole transducer principle comprise, or are constructed based on, the basic structure shown in FIG. 1. For example, it represents the basic structure of the semiconductor sensor in SE 387444. A prior art hydrogen gas sensitive semiconductor sensor working based on the hydrogen dipole transducer principle comprises a catalytic metal layer 1, a semiconductor layer 2 and an insulator layer 3 arranged between the catalytic metal layer 1 and the semiconductor layer 2. The catalytic metal layer 1 comprises an outer surface 4 arranged to be in physical contact with and to freely communicate with the ambient atmosphere, i.e. the atmosphere surrounding the sensor or the atmosphere surrounding the catalytic metal layer 1. Thus, the outer surface 4 defines the bounds of the catalytic metal layer 1 to the ambient atmosphere and is arranged to adsorb hydrogen gas molecules from the ambient atmosphere and dissociate adsorbed hydrogen gas molecules. The outer surface 4 comprises all surface parts of the catalytic metal layer 1 arranged to be in physical contact with and to freely communicate with the ambient atmosphere.

In addition, the catalytic metal layer 1 has an upper surface 5 and a side surface 6, whereby the terms "upper" and "side" are used to indicate the positions of the surface 5 and the surface 6, respectively, when the basic structure of the semiconductor sensor has the orientation shown in FIG. 1. Thus, when the basic structure of the semiconductor sensor has the orientation shown in FIG. 1, the side surface 6 is the surface of the catalytic metal layer 1 defining the bounds of the catalytic metal layer 1 in the horizontal direction. The catalytic metal layer 1 comprises the side surface 6 due to that the catalytic metal layer 1 has a certain thickness. In prior art hydrogen gas sensitive semiconductor sensors working based on the hydrogen dipole transducer principle, the complete upper surface 5 and the complete side surface 6 are arranged to be in physical contact with and to freely communicate with the ambient atmosphere. Accordingly, since the outer surface 4 comprises all surface parts of the catalytic metal layer 1 arranged to be in physical contact with and to freely communicate with the ambient atmosphere, the outer surface 4 then comprises the complete upper surface 5 as well as the complete side surface 6.

Furthermore, the catalytic metal layer 1 comprises an inner surface 7, which is arranged to not be in physical contact with and to not freely communicate with the ambient atmosphere, i.e. it may not adsorb hydrogen gas molecules from the ambient atmosphere. In known hydrogen gas sensitive semiconductor sensors working based on the hydrogen dipole transducer principle and having the basic structure shown in FIG. 1, the surface area of the upper surface 5 is essentially equal to the surface area of the inner surface 7. However, the surface area of the outer surface 4 is also essentially equal to the surface area of the inner surface 7 in spite of the fact that the outer surface 4 comprises the upper surface 5 as well as the side surface 6. This is due to that the catalytic metal layer 1 is very thin, whereby the surface area of the side surface 6 is very small compared to the surface area of the upper surface 5. Normally, the catalytic metal layer 1 is produced by thin film technique.

The inner surface 7 of prior art sensors comprises a hydrogen atom adsorption surface portion 8, which bears on, or is at least arranged adjacent to, the insulator layer 3, i.e. there are no further components between the hydrogen atom adsorption surface portion 8 and the insulator layer 3. The term "hydrogen atom adsorption surface portion" refers herein to a surface portion which bears on, or is at least arranged adjacent to, the insulator layer 3. Hydrogen atoms may be adsorbed at a hydrogen atom adsorption surface portion 8, or more specifically, hydrogen atoms may be adsorbed at adsorption sites for hydrogen atoms at the interface between a hydrogen atom adsorption surface portion 8 and the insulator layer 3.

In prior art sensors the hydrogen atom adsorption surface portion 8 constitutes about 55% of the inner surface 7. Therefore, about 55% of the inner surface 7 bears on, or is at least arranged adjacent to, the insulator layer 3. The remaining surface portion(s) of the inner surface 7, i.e. about 45% of the inner surface 7, is/are arranged adjacent to contact frames and the like (not shown). Thus, since the surface areas of the outer surface 4 and the inner surface 7 are essentially equal, the surface area of the outer surface 4 of a prior art sensor is about 80% larger than the surface area of the hydrogen atom adsorption surface portion 8.

For purposes of illustration, a hydrogen gas molecule is denoted H-H and a hydrogen atom is denoted H in FIG. 1.

The basic working principle of a hydrogen gas sensitive semiconductor sensor having the basic structure shown in FIG. 1 will now be described. When hydrogen gas molecules are present in the atmosphere surrounding a hydrogen gas sensitive semiconductor sensor having the basic structure shown in FIG. 1, some of them may adsorb on the outer surface 4 of the catalytic metal layer 1. The adsorbed hydrogen gas molecules may then be dissociated on the outer surface 4 and the hydrogen atoms thus formed may be absorbed into the catalytic metal layer 1. Some of the absorbed hydrogen atoms will subsequently be adsorbed at the interface between the catalytic metal layer 1 and the insulator layer 3, i.e. at the hydrogen atom adsorption surface portion 8 of the inner surface 7 of the catalytic metal layer 1, after diffusion through the catalytic metal layer 1.

Figure 2:
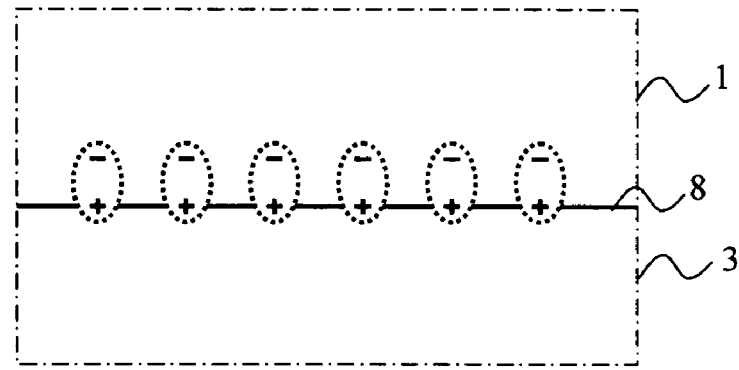
FIG. 2 shows schematically hydrogen dipoles generated at an interface between a catalytic metal layer and an insulator layer of a gas sensitive semiconductor sensor working based on the hydrogen dipole transducer principle.

Hydrogen atoms adsorbed at the interface between the catalytic metal layer 1 and the insulator layer 3, i.e. at the hydrogen atom adsorption surface portion 8 of the inner surface 7, are polarized, whereby hydrogen dipoles are produced. This is schematically illustrated in FIG. 2. The hydrogen dipoles generate an electrical field that shifts the effective work function of the catalytic metal layer 1. In consequence of the shift of the effective work function of the catalytic metal layer 1, the electrical function of the semiconductor sensor is influenced, i.e. a voltage shift in the characteristics of the semiconductor sensor is generated, and this influence may be utilized for the detection of presence of hydrogen gas molecules and/or measurement of the concentration of hydrogen gas molecules in a gas sample. The magnitude of the shift is determined by the number of hydrogen atoms adsorbed per unit area, i.e. the density of hydrogen dipoles, at the hydrogen atom adsorption surface portion 8, or more specifically at the interface between the hydrogen atom adsorption surface portion 8 and the insulator layer 3.

The amount of hydrogen gas molecules in the atmosphere surrounding the sensor and the density of hydrogen dipoles at the hydrogen atom adsorption surface portion 8 equilibrate after a certain time and the equilibrium shift of the effective work function of the catalytic metal layer 1 may be utilized for measurement of the concentration of hydrogen gas molecules in the atmosphere surrounding the sensor, i.e. in a gas sample. However, the time before equilibrium is achieved between the amount of hydrogen gas molecules in the atmosphere surrounding the sensor and the density of hydrogen dipoles at the hydrogen atom adsorption surface portion 8 is usually relatively long. For that reason, it is preferred to utilize the rate with which the effective work function is shifted, i.e. the rate with which the output signal is shifted, before an equilibrium shift is achieved, for measurement of the concentration of hydrogen gas molecules in the atmosphere surrounding the sensor, i.e. in a gas sample.

It is common that prior art hydrogen gas sensitive semiconductor sensors working based on the hydrogen dipole transducer principle is implemented as a field-effect transistor. Then hydrogen atoms may be adsorbed at the complete hydrogen atom adsorption surface portion 8 of the inner surface 7 of the catalytic metal layer 1, but only those hydrogen atoms adsorbed at the part of the hydrogen atom adsorption surface portion 8 arranged at the channel will influence the voltage shift in the characteristics of the sensor. This will be further described below.

FIGS. 3-6 show the basic structure of different embodiments of a hydrogen gas sensitive semiconductor sensor according to the present invention, which works based on the hydrogen dipole transducer principle. The hydrogen gas sensitive semiconductor sensor according to the invention comprises in all embodiments a catalytic metal layer 1, a semiconductor layer 2 and an insulator layer 3 arranged between the catalytic metal layer 1 and the semiconductor layer 2. The catalytic metal layer 1 comprises an outer surface 4 arranged to be in physical contact with and to freely communicate with the ambient atmosphere, i.e. the atmosphere surrounding the sensor or the atmosphere surrounding the catalytic metal layer 1. Thus, the outer surface 4 defines the bounds of the catalytic metal layer 1 to the ambient atmosphere and is arranged to adsorb hydrogen gas molecules from the ambient atmosphere and dissociate adsorbed hydrogen gas molecules. The outer surface 4 comprises all surface parts of the catalytic metal layer 1 arranged to be in physical contact with and to freely communicate with the ambient atmosphere.

The term "catalytic metal" is herein used to denote a metal or an alloy being capable to dissociate hydrogen gas molecules and to absorb the hydrogen atoms thus formed. In accordance with this definition, non-limiting examples of the catalytic metal in the catalytic metal layer 1 of a sensor according to the invention are any of the platinum metals palladium, platinum and iridium or an alloy comprising at least one of these metals. Non-limiting examples of alloys that may constitute the catalytic metal is an alloy comprising silver and palladium or an alloy comprising nickel and palladium.

The catalytic metal layer 1 of the sensor according to the invention has an upper surface 5 and a side surface 6, whereby the terms "upper" and "side" are used to indicate the positions of the surface 5 and the surface 6, respectively, when the basic structure of the sensor has the orientation shown in FIGS. 3-6. Preferably, the outer surface 4 of a sensor according to the invention comprises both the complete upper surface 5 and the complete side surface 6. However, the side surface 6 may in variants be completely or partly covered by some other component(s) of the sensor such that it is completely or partly restricted from freely communicating with the ambient atmosphere. Then the outer surface 4 comprises the upper surface 5 and that part/those parts, if any, of the side surface 6 being arranged to freely communicate with the ambient atmosphere.

Furthermore, the catalytic metal layer 1 comprises an inner surface 7, which is arranged to not be in physical contact with and to not freely communicate with the ambient atmosphere, i.e. it may not adsorb hydrogen gas molecules from the ambient atmosphere. In the sensor according to the present invention, the inner surface 7 comprises at least one hydrogen atom adsorption surface portion 8. Each hydrogen atom adsorption surface portion 8 is arranged adjacent to, or bears on, the insulator layer 3, i.e. there are no further components between a hydrogen atom adsorption surface portion 8 and the insulator layer 3. Thus, in the sensor according to the invention, the inner surface 7 may comprise one hydrogen atom adsorption surface portion 8 (FIGS. 3-4 and FIG. 6) or more than one hydrogen atom adsorption surface portion 8 (FIG. 5). The inner surface 7 of prior art hydrogen gas sensitive semiconductor sensors working based on the hydrogen dipole transducer principle comprise only one hydrogen atom adsorption surface portion 8 (FIG. 1). Furthermore, as in prior art sensors, the inner surface 7 of the sensor according to the invention comprises also one or several surface portions arranged adjacent to contact frames and the like (not shown). For example, the total surface area of the surface portion(s) arranged adjacent to contact frames and the like may constitute, as in prior art sensors, about 45% of the surface area of the inner surface 7. However, the percentage that the total surface area of the surface portion(s) arranged adjacent to contact frames and the like constitutes of the surface area of the inner surface 7 may be varied.

Furthermore, in the sensor according to the present invention the ratio of the surface area of the outer surface 4 to the total surface area of all hydrogen atom adsorption surface portions 8 of the inner surface 7 is substantially augmented compared to that ratio in prior art hydrogen gas sensitive semiconductor sensors working based on the hydrogen dipole transducer principle. In prior art sensors, the surface area of the outer surface 4 is, as mentioned above, about 80% larger than the total surface area of all hydrogen atom adsorption surface portions 8, i.e. the one hydrogen atom adsorption surface portion 8.

The fact that the ratio of the surface area of the outer surface 4 to the total surface area of all hydrogen atom adsorption surface portions 8 of the inner surface 7 is substantially augmented in the sensor according to the invention compared to that ratio in prior art sensors implies that the ratio of the number of sites arranged for adsorption and dissociation of hydrogen gas molecules on the outer surface 4 to the total number of sites arranged for adsorption of hydrogen atoms at the hydrogen atom adsorption surface portion(s) 8 of the inner surface 7 is substantially augmented in the sensor according to the invention compared to that ratio in prior art sensors.

Thereby, the sensor according to the invention may provide a substantially higher number of hydrogen atoms adsorbed per unit area, i.e. a higher density of dipoles, at the hydrogen atom adsorption surface portion(s) 8 of the inner surface 7, at a certain concentration of hydrogen gas in a gas sample, than prior art sensors at an initial use. Thus, the sensor according to the invention has a substantially higher initial sensitivity than prior art sensors and a hydrogen gas sensitive semiconductor sensor with a substantially increased initial sensitivity is provided according to the invention.

As mentioned above, the sensitivity of hydrogen gas sensitive semiconductor sensors working based on the hydrogen dipole transducer principle typically decays with sensor age due to that oxygen and/or other contaminating substances adsorb on, or bond to, the outer surface 4 of the catalytic metal layer 1. Thereby, the life of hydrogen gas sensitive semiconductor sensors working based on the hydrogen dipole transducer principle is substantially reduced due to that oxygen and/or other contaminating substances adsorb on, or bond to, the outer surface 4 of the catalytic metal layer 1.

However, the fact that the initial sensitivity of the sensor according to the invention is substantially increased compared to the initial sensitivity of prior art sensors implies also that the life of the sensor according to the invention is substantially increased compared to the life of prior art sensors. That fact should be apparent for a person skilled in the art. The substantial augmentation of the ratio of the number of sites arranged for adsorption and dissociation of hydrogen gas molecules on the outer surface 4 to the total number of sites arranged for adsorption of hydrogen atoms at the hydrogen atom adsorption surface portion(s) 8 of the inner surface 7 in the sensor according to the invention implies that the time is substantially lengthened before oxygen and/or other contaminants have occupied that many sites on the outer surface 4 that the sensitivity is reduced to such a degree that the sensor no longer is useable. Thereby, the life of the sensor according to the invention is substantially increased compared to the life of prior art sensors.

Thus, according to the invention, any of the measures described above for increasing the life of a hydrogen gas sensitive semiconductor sensor, i.e. purification of gas samples from oxygen and other contaminating substances, use of equipment for modification of the atmosphere surrounding the semiconductor sensor or modification of the catalytic property of the catalytic metal layer, are not required for obtaining an increased life of a hydrogen gas sensitive semiconductor sensor working based on the hydrogen dipole transducer principle. However, if the sensor according to the invention is combined with any of such measures, an even more increased life may be achieved.

Depending on the application of the sensor according to the invention, the advantage of the sensor may be the increased initial sensitivity, the increased life or a combination of both.

Furthermore, when comparing a prior art sensor and a sensor according to the invention after a certain time period of use but before oxygen and/or other contaminants have reduced the sensitivity of any of them to such a degree that the sensor no longer is useable, the ratio of the number of sites that still are free for adsorption and dissociation of hydrogen gas molecules on the outer surface 4 to the total number of sites arranged for adsorption of hydrogen atoms at the hydrogen atom adsorption surface portion(s) 8 is substantially higher in the sensor according to the invention than in the prior art sensor. Thereby, the sensor according to the invention may still provide a substantially higher density of dipoles at the hydrogen atom adsorption surface portion(s) 8 of the inner surface 7, at a certain concentration of hydrogen gas in a gas sample, than the prior art sensor after a certain time period of use but before oxygen and/or other contaminants have reduced the sensitivity of any of them to such a degree that the sensor no longer is useable. Thus, the sensor according to the invention has a substantially higher sensitivity than the prior art sensor when they are compared after a certain time period of use, but before the sensitivity of any of them is reduced to such a degree that it no longer is useable.

Furthermore, by varying the ratio of the surface area of the outer surface 4 to the total surface area of all hydrogen atom adsorption surface portions 8 of the inner surface 7 in the sensor according to the invention, the initial sensitivity may be tailored in order to achieve a desired initial sensitivity.

The augmentation of the ratio of the surface area of the outer surface 4 to the total surface area of all hydrogen atom adsorption surface portions 8 of the inner surface 7 of the sensor according to the invention compared to that ratio in prior art sensors implies that the costs for production of the sensor according to the invention are increased. This will be apparent below. In order to accomplish an effect, i.e. an increase of the initial sensitivity, which is large enough to be interesting with regard to the increased production costs, the surface area of the outer surface 4 has to be at least 100% larger than the total surface area of all of the at least one hydrogen atom adsorption surface portion 8 of the inner surface 7 of the sensor according to the invention. Thus, in the hydrogen gas sensitive semiconductor sensor according to the present invention, the surface area of the outer surface 4 is at least 100% larger than the total surface area of all of the at least one hydrogen atom adsorption surface portion 8 of the inner surface 7.

Furthermore, the larger the augmentation, the higher the initial sensitivity. However, the production costs are typically increased if the augmentation is increased. Thereby the advantages of the increase of the initial sensitivity and the increased production costs have to be weighed against each other when choosing the ratio of the surface area of the outer surface 4 to the total surface area of all of the at least one hydrogen atom adsorption surface portion 8. For some applications it is preferred, or necessary, to assign a very high initial sensitivity to the sensor in order to enable measurement of a very low concentration of hydrogen gas molecules in a gas sample. Then it may, for example, be preferred that the surface area of the outer surface 4 is at least 500% larger than the total surface area of all of the at least one hydrogen atom adsorption surface portion 8 of the inner surface 7. For other applications it is preferred, or necessary, to assign an extremely high initial sensitivity to the sensor in order to enable measurement of an extremely low concentration of hydrogen gas molecules in a gas sample. Then it may, for example, be preferred that the surface area of the outer surface 4 is at least 5000% larger than the total surface area of all of the at least one hydrogen atom adsorption surface portion 8 of the inner surface 7.

Figure 3:
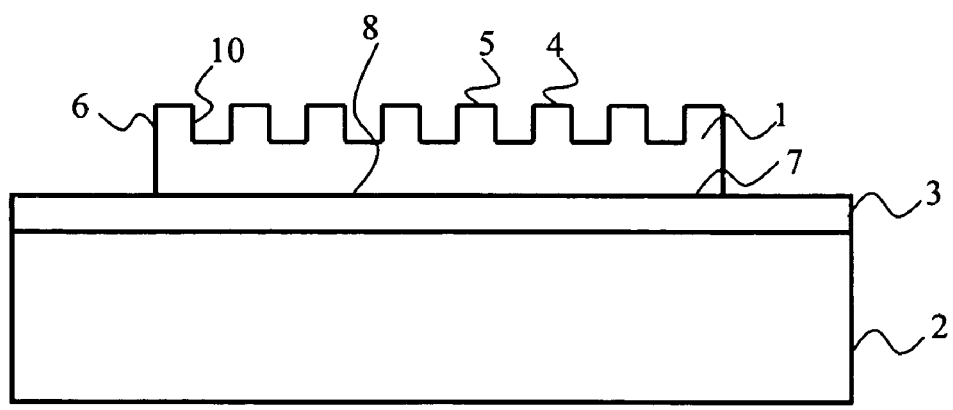
FIG. 3 is a schematic cross-sectional view of the basic structure of a first embodiment of a hydrogen gas sensitive semiconductor sensor according to the present invention.

FIG. 3 shows a schematic cross-sectional view of the basic structure of a first embodiment of the sensor according to the invention. In the first embodiment, the inner surface 7 comprises one hydrogen atom adsorption surface portion 8, which bears on, or is at least arranged adjacent to, the insulator layer 3, i.e. there are no further components between the hydrogen atom adsorption surface portion 8 and the insulator layer 3. As mentioned above, the term "hydrogen atom adsorption surface portion" refers herein to a surface portion which bears on, or is at least arranged adjacent to, the insulator layer 3. Hydrogen atoms may be adsorbed at a hydrogen atom adsorption surface portion 8, or more specifically, hydrogen atoms may be adsorbed at adsorption sites for hydrogen atoms at the interface between a hydrogen atom adsorption surface portion 8 and the insulator layer 3.

Furthermore, a surface-enlarging structure 10 is assigned to the upper surface 5 of the first embodiment, which structure 10 is arranged to imply that the ratio of the surface area of the outer surface 4 to the surface area of the hydrogen atom adsorption surface portion 8 of the inner surface 7 is substantially augmented compared to that ratio in prior art sensors. More specifically, the assigned surface-enlarging structure 10 is tailored such that it implies that the surface area of the outer surface 4 is at least 100% larger than the surface area of the hydrogen atom adsorption surface portion 8 of the inner surface 7. For some applications, the assigned surface-enlarging structure 10 is tailored such that it implies that the surface area of the outer surface 4 is at least 500% larger than the surface area of the hydrogen atom adsorption surface portion 8 of the inner surface 7 and for other applications it is tailored such that the surface area of the outer surface 4 is at least 5000% larger than the surface area of the hydrogen atom adsorption surface portion 8 of the inner surface 7.

The specific structure of the surface-enlarging structure 10 shown in FIG. 3 is only one example of a possible structure of a surface-enlarging structure 10 that may be assigned to the upper surface 5 in order to geometrically enlarge the outer surface 4. Thus, in variants of the first embodiment, the surface-enlarging structure 10 has another specific structure, whereby another structure is assigned to the upper surface 5 than that shown in FIG. 3. For example, the surface-enlarging structure 10 may be wave-shaped. The surface-enlarging structure 10 may also be irregular.

A surface-enlarging structure 10 may be assigned to the upper surface 5 by, for example, photolithographic methods, whereby a pattern first is defined by photo technique and thereafter produced by an etching method or a sputtering/blasting method.

Another way (not shown) of assigning a surface-enlarging structure 10 to the upper surface 5 is to design the sensor such that the catalytic metal layer 1 is porous at the uppermost partial layer(s), whereby the term "uppermost" is utilized to indicate the position of the mentioned partial layer(s) in the catalytic metal layer 1 when the basic structure of the sensor according to the invention has the orientation shown in FIG. 3. Then the porosity of the uppermost partial layer(s) implies that the upper surface 5 is assigned a surface-enlarging structure 10. Porosity of the uppermost partial layer(s) may, for example, be achieved by etching, plating or vapour deposition.

When comparing a prior art sensor and a sensor according to the first embodiment of the invention, which sensors only differ in that the surface area of the outer surface 4 of the sensor according to the first embodiment of the invention is essentially larger due to the surface-enlarging structure 10 than the surface area of the outer surface 4 of the prior art sensor, the sensor according to the first embodiment of the invention has substantially more sites arranged for adsorption and dissociation of hydrogen gas molecules compared to the prior art sensor. Thereby, a substantially higher number of hydrogen gas molecules may be adsorbed and dissociated at a certain concentration of hydrogen gas molecules in a gas sample by the sensor according to the first embodiment of the invention than by the prior art sensor at an initial use. This implies that a substantially higher number of hydrogen atoms may be adsorbed per unit area at the hydrogen atom adsorption surface portion 8, at a certain concentration of hydrogen gas molecules in a gas sample, in the sensor according to the first embodiment of the invention than in the prior art sensor at an initial use. Consequently, the initial sensitivity of the sensor according to the first embodiment of the invention is substantially higher than the initial sensitivity of the prior art sensor. In accordance with that mentioned above, the life of the sensor according to the first embodiment of the invention is then also substantially longer than the life of the prior art sensor. Furthermore, the sensor according to the first embodiment of the invention has not only initially a substantially higher sensitivity than the prior art sensor. When the prior art sensor and the sensor according to the first embodiment of the invention are compared after a certain time period of use, but before the sensitivity of any of the sensors is reduced by oxygen and other contaminants to such a degree that the sensor no longer is useable, the sensor according to the first embodiment of the invention has still a substantially higher sensitivity than the prior art sensor.

Figure 4A:
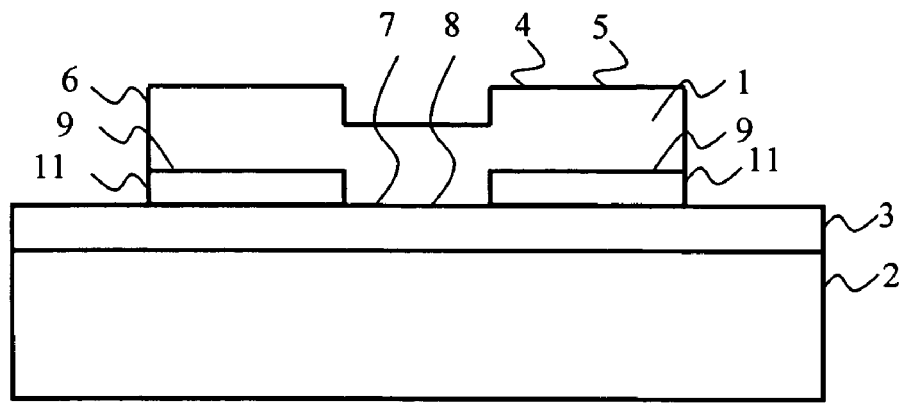
FIG. 4a is a schematic cross-sectional view of the basic structure of a second embodiment of the hydrogen gas sensitive semiconductor sensor according to the present invention.
Figure 4B:
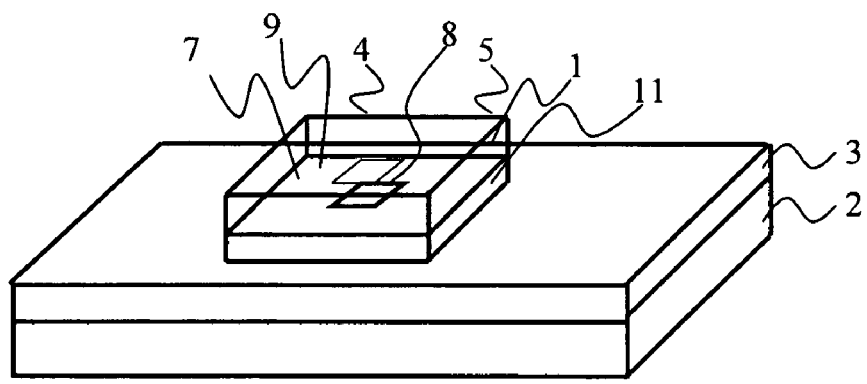
FIG. 4b is a schematic perspective view of the basic structure of a second embodiment of the hydrogen gas sensitive semiconductor sensor according to the present invention.
Figure 5:
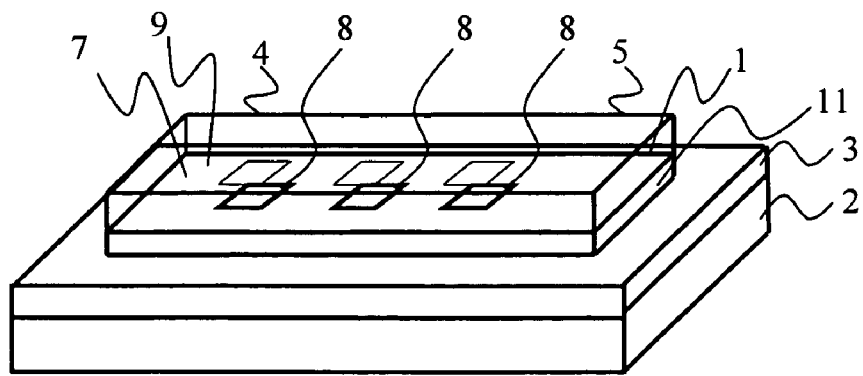
FIG. 5 is a schematic perspective view of the basic structure of a third embodiment of the hydrogen gas sensitive semiconductor sensor according to the present invention.

FIG. 4*a* and 4*b* show a schematic cross-sectional view and a schematic perspective view, respectively, of the basic structure of a second embodiment of the sensor according to the invention. In the second embodiment, the upper surface 5 comprises no surface-enlarging structure 10 as the upper surface 5 in the first embodiment. Furthermore, the surface areas of the inner surface 7 and the outer surface 4 are essentially equal. The inner surface 7 comprises in the second embodiment one hydrogen atom adsorption surface portion 8 bearing on, or being arranged adjacent to, the insulator layer 3. Furthermore, the inner surface 7 comprises a hydrogen atom adsorption inhibited surface portion 9 not being arranged adjacent to, or bearing on, the insulator layer 3.

The term "hydrogen atom adsorption inhibited surface portion" refers herein to a surface portion, which does not bear on, nor is arranged adjacent to, the insulator layer 3. Hydrogen atoms may not, or at least essentially not, be adsorbed at a hydrogen atom adsorption inhibited surface portion 9. A hydrogen atom adsorption inhibiting material layer 11 is sandwiched between the hydrogen atom adsorption inhibited surface portion 9 and the insulator layer 3 such that the complete hydrogen atom adsorption inhibited surface portion 9 bears on, or is arranged adjacent to, the hydrogen atom adsorption inhibiting material layer 11. The term "hydrogen atom adsorption inhibiting material" refers herein to a material comprising no or very few sites for adsorption of hydrogen atoms. The hydrogen atom adsorption inhibiting material layer 11 inhibits substantially adsorption of hydrogen atoms at the hydrogen atom adsorption inhibited surface portion 9, or more specifically it inhibits substantially hydrogen atoms from being adsorbed at the interface between the hydrogen atom adsorption inhibited surface portion 9 and the hydrogen atom adsorption inhibiting material layer 11. Thus, no, or essentially no, hydrogen atoms may be adsorbed at the hydrogen atom adsorption inhibited surface portion 9, or more specifically no or essentially no hydrogen atoms may be adsorbed at the interface between the hydrogen atom adsorption inhibited surface portion 9 and the hydrogen atom adsorption inhibiting material layer 11. Even if adsorption of hydrogen atoms at the hydrogen atom adsorption inhibited surface portion 9 is not completely inhibited, i.e. if it is only essentially inhibited, whereby a few hydrogen atoms may be adsorbed at the hydrogen atom adsorption inhibited surface portion 9, it is inhibited compared to the adsorption of hydrogen atoms at the hydrogen atom adsorption surface portion 8. Thereby, even if a few hydrogen atoms may be adsorbed at the hydrogen atom adsorption inhibited surface portion 9, it is herein denoted as being hydrogen atom adsorption inhibited.

The hydrogen atom adsorption inhibiting material is preferably a non-catalytic metal or a non-catalytic alloy. For example, the hydrogen atom adsorption inhibiting material is aluminium, an aluminium alloy or chromium. The thickness of the hydrogen atom adsorption inhibiting material layer 11 is 0.001-0.3 µm.

The surface area of the hydrogen atom adsorption inhibited surface portion 9 in the second embodiment of the sensor according to the invention is tailored such that it implies that the ratio of the surface area of the outer surface 4 to the surface area of the hydrogen atom adsorption surface portion 8 is substantially augmented compared to that ratio in prior art sensors. More specifically, the surface area of the hydrogen atom adsorption inhibited surface portion 9 is tailored such that it implies that the surface area of the outer surface 4 is at least 100% larger than the surface area of the hydrogen atom adsorption surface portion 8 of the inner surface 7. For some applications, it is tailored such that the surface area of the outer surface 4 is at least 500% larger than the surface area of the hydrogen atom adsorption surface portion 8 of the inner surface 7 and for other applications it is tailored such that the surface area of the outer surface 4 is at least 5000% larger than the surface area of the hydrogen atom adsorption surface portion 8 of the inner surface 7. The surface area of the hydrogen atom adsorption inhibited surface portion 9 is tailored by tailoring the surface area of the hydrogen atom adsorption inhibiting material layer 11 that the hydrogen atom adsorption inhibited surface portion 9 bears on, or is arranged adjacent to.

When comparing a prior art sensor and a sensor according to the second embodiment of the invention, which sensors only differ in that the inner surface 7 of the sensor according to the invention comprises a hydrogen atom adsorption inhibited surface portion 9, (i.e. each sensor has one hydrogen atom adsorption surface portion 8 and the sensors have, for example, equal surface areas of the inner surface 7, equal surface areas of the outer surface 4 and equal percentages of the inner surface 7 that is arranged adjacent to contact frames and the like), the hydrogen atom adsorption surface portion 8 of the sensor according to the second embodiment of the invention is substantially smaller than the hydrogen atom adsorption surface portion 8 of the prior art sensor. Thus, the sensor according to the second embodiment of the invention has sites for adsorption of hydrogen atoms at a substantially smaller surface area of the inner surface 7 than the prior art sensor. Thereby, even though the prior art sensor and the sensor according to the second embodiment of the invention have equal surface areas of the outer surface 4 and thus equal number of sites arranged for adsorption and dissociation of hydrogen gas molecules, a substantially higher density of hydrogen dipoles may be achieved at the hydrogen atom adsorption surface portion 8 in the sensor according to the second embodiment of the invention than in the prior art sensor at a certain concentration of hydrogen gas in a gas sample. Consequently, the initial sensitivity of the sensor according to the second embodiment of the invention is substantially higher than the initial sensitivity of the prior art sensor. In accordance with that mentioned above, the life of the sensor according to the second embodiment of the invention is then also substantially longer than the life of the prior art sensor. Furthermore, the sensor according to the second embodiment of the invention has not only initially a substantially higher sensitivity than the prior art sensor. When the prior art sensor and the sensor according to the second embodiment of the invention are compared after a certain time period of use, but before the sensitivity of any of the sensors is reduced to such a degree by oxygen and other contaminants that the sensor no longer is useable, the sensor according to the second embodiment of the invention has still a substantially higher sensitivity than the prior art sensor.

In the first and second embodiments of the sensor according to the invention, the inner surface 7 comprises one hydrogen atom adsorption surface portion 8. However, in other embodiments, as mentioned above, the inner surface 7 may comprise more than one hydrogen atom adsorption surface portion 8.

FIG. 5 shows a schematic perspective view of the basic structure of a third embodiment of the sensor according to the invention, in which the inner surface 7 comprises three hydrogen atom adsorption surface portions 8 bearing on, or arranged adjacent to, the insulator layer 3 and one hydrogen atom adsorption inhibited surface portion 9 bearing on, or arranged adjacent to, a hydrogen atom adsorption inhibiting material layer 11. In the third embodiment, the upper surface 5 comprises no surface-enlarging structure 10. Furthermore, the surface areas of the inner surface 7 and the outer surface 4 are essentially equal.

In the third embodiment, the surface area of the hydrogen atom adsorption inhibited surface portion 9 is tailored such that it implies that the ratio of the surface area of the outer surface 4 to the total surface area of all hydrogen atom adsorption surface portions 8, i.e. the three hydrogen atom adsorption surface portions 8, is substantially augmented compared to that ratio in prior art sensors. More specifically, the surface area of the hydrogen atom adsorption inhibited surface portion 9 is tailored such that it implies that the surface area of the outer surface 4 is at least 100% larger than the total surface area of the three hydrogen atom adsorption surface portions 8 of the inner surface 7. For some applications, it is tailored such that the surface area of the outer surface 4 is at least 500% larger than the total surface area of the three hydrogen atom adsorption surface portions 8 of the inner surface 7 and for other applications it is tailored such that the surface area of the outer surface 4 is at least 5000% larger than the total surface area of the three hydrogen atom adsorption surface portions 8 of the inner surface 7. The surface area of the hydrogen atom adsorption inhibited surface portion 9 is tailored by tailoring the surface area of the hydrogen atom adsorption inhibiting material layer 11 that the hydrogen atom adsorption inhibited surface portion 9 bears on, or is arranged adjacent to.

In variants (not shown) of the third embodiment, the inner surface 7 comprises other numbers of hydrogen atom adsorption surface portions 8 than in the third embodiment. The inner surface 7 may in such variants comprise any suitable number of hydrogen atom adsorption surface portions 8.

Figure 6:
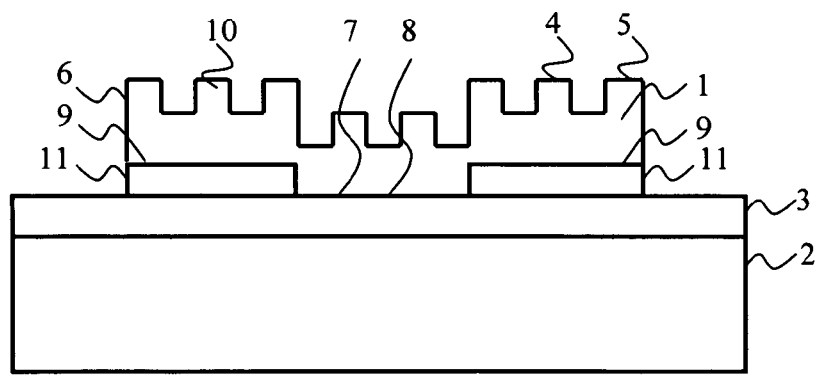
FIG. 6 is a schematic cross-sectional view of the basic structure of a fourth embodiment of the hydrogen gas sensitive semiconductor sensor according to the present invention.

FIG. 6 shows a schematic cross-sectional view of the basic structure of a fourth embodiment of the sensor according to the invention, which is a combination of the first and the second embodiments. The inner surface 7 of the sensor comprises in the fourth embodiment one hydrogen atom adsorption surface portion 8 bearing on, or arranged adjacent to, the insulator layer 3 and one hydrogen atom adsorption inhibited surface portion 9 bearing on, or arranged adjacent to, a hydrogen atom adsorption inhibiting material layer 11. Furthermore, the upper surface 5 is assigned a surface-enlarging structure 10.

The assigned surface-enlarging structure 10 and the surface area of the hydrogen atom adsorption inhibited surface portion 9 are tailored such that they imply that the ratio of the surface area of the outer surface 4 to the surface area of the hydrogen atom adsorption surface portion 8 is substantially augmented compared to that ratio in prior art sensors. More specifically, the assigned surface-enlarging structure 10 and the surface area of the hydrogen atom adsorption inhibited surface portion 9 are tailored such that they imply that the surface area of the outer surface 4 is at least 100% larger than the surface area of the hydrogen atom adsorption surface portion 8 of the inner surface 7. For some applications, they are tailored such that the surface area of the outer surface 4 is at least 500% larger than the surface area of the hydrogen atom adsorption surface portion 8 of the inner surface 7 and for other applications they are tailored such that the surface area of the outer surface 4 is at least 5000% larger than the surface area of the hydrogen atom adsorption surface portion 8 of the inner surface 7.

In variants (not shown) of the fourth embodiment, the inner surface 7 comprises other numbers of hydrogen atom adsorption surface portions 8 than in the fourth embodiment. The inner surface 7 may in such variants comprise any suitable number of hydrogen atom adsorption surface portions 8.

Furthermore, in the second, third and fourth embodiments, the inner surface 7 comprises one hydrogen atom adsorption inhibited surface portion 9. However, in other embodiments (not shown) the inner surface 7 may comprise more than one hydrogen atom adsorption inhibited surface portion 9. A hydrogen atom adsorption inhibiting material layer 11 is then sandwiched between each hydrogen atom adsorption inhibited surface portion 9 and the insulator layer 3. Each hydrogen atom adsorption inhibited surface portion 9 is arranged adjacent to a hydrogen atom adsorption inhibiting material layer 11. If the inner surface 7 comprises at least two hydrogen atom adsorption inhibited surface portions 9 and thereby at least two hydrogen atom adsorption inhibiting material layers 11 are arranged between the catalytic metal layer 1 and the insulator layer 3, all of the at least two hydrogen atom adsorption inhibiting material layers 11 may be of the same hydrogen atom adsorption inhibiting material or at least two of the hydrogen atom adsorption inhibiting material layers 11 may be of different hydrogen atom adsorption inhibiting materials. Furthermore, in embodiments having more than one hydrogen atom adsorption inhibited surface portion 9, the upper surface 5 may be assigned a surface-enlarging structure 10. However, in some embodiments having more than one hydrogen atom adsorption inhibited surface portion 9, the upper surface 5 is not assigned a surface-enlarging structure 10. Furthermore, embodiments having more than one hydrogen atom adsorption inhibited surface portion 9 may comprise any suitable number of hydrogen atom adsorption surface portions 8. However, the sensor according to the invention comprises of course at least one hydrogen atom adsorption surface portion 8.

Thus, a sensor according to the invention may comprise any suitable number of hydrogen atom adsorption surface portions 8 and any suitable number of hydrogen atom adsorption inhibited surface portions 9. However, the sensor comprises of course at least one hydrogen atom adsorption surface portion 8, whereas it may comprise none, one or more than one hydrogen atom adsorption inhibited surface portion 9. Furthermore, a sensor according to the invention may comprise any suitable number of hydrogen atom adsorption surface portions 8 and any suitable number of hydrogen atom adsorption inhibited surface portions 9 in combination with an upper surface 5 being assigned a surface-enlarging structure 10 or in combination with an upper surface 5 not being assigned a surface-enlarging structure 10.

The hydrogen gas sensitive semiconductor sensor according to the invention may be utilized for detection of hydrogen gas in the atmosphere surrounding the sensor, i.e. it may be utilized for detection of hydrogen gas in a gas sample or volume sample of gas. More specifically, the hydrogen gas sensitive semiconductor sensor according to the invention may be utilized for detection of presence of hydrogen gas molecules in a gas sample and/or measurement of the concentration of hydrogen gas molecules in a gas sample.

Figure 7:
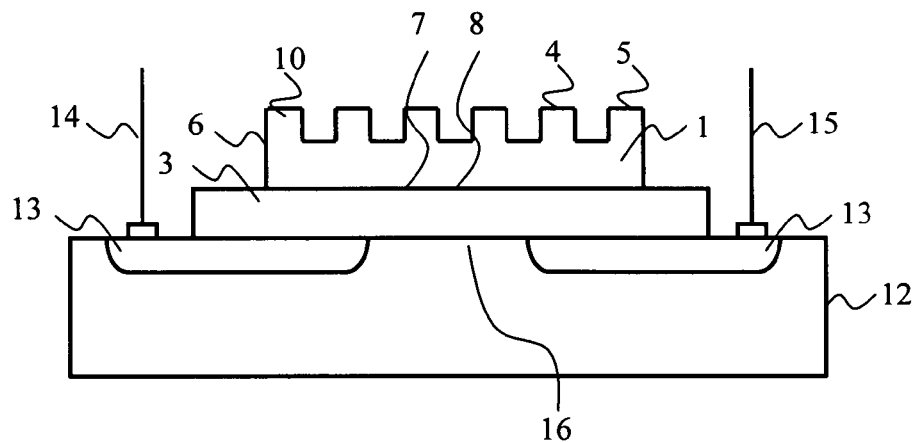
FIG. 7 is a schematic cross-sectional view of the basic structure of a field-effect transistor comprising the basic structure of the first embodiment of the hydrogen gas sensitive semiconductor sensor according to the invention.
Figure 8:
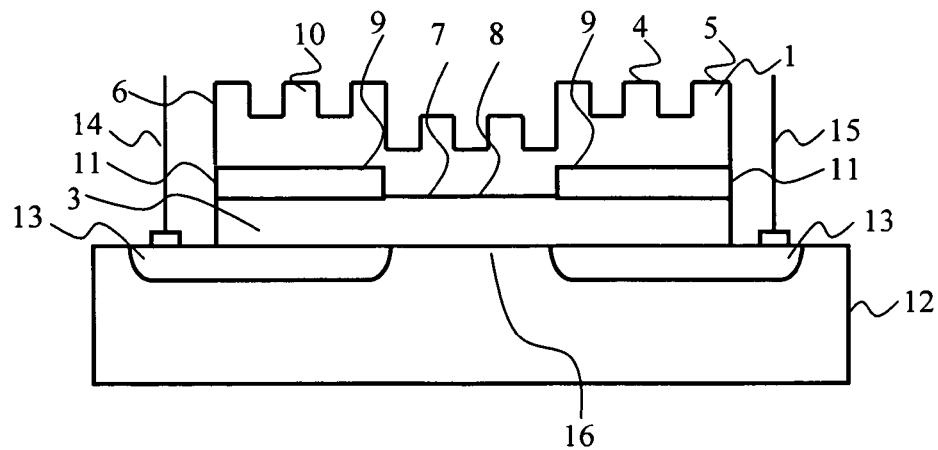
FIG. 8 is a schematic cross-sectional view of the basic structure of a field-effect transistor comprising the basic structure of the fourth embodiment of the hydrogen gas sensitive semiconductor sensor according to the invention.

The hydrogen gas sensitive semiconductor sensor according to the invention may, for example, be implemented as a metal-insulator-semiconductor field-effect device or a Schottky-barrier device. Any embodiment of the hydrogen gas sensitive semiconductor sensor according to the invention may be implemented as a metal-insulator-semiconductor field-effect device or Schottky-barrier device. The implementation of a hydrogen gas sensitive semiconductor sensor according to the invention as a metal-insulator-semiconductor field-effect device or a Schottky-barrier device should be apparent for a person skilled in the art. For example, the hydrogen gas sensitive semiconductor sensor according to the invention may be implemented as a field-effect transistor. FIGS. 7 and 8 show two examples of the implementation of the sensor according to the invention as a field-effect transistor, which two examples comprise different embodiments of the sensor according to the invention. However, in accordance with that mentioned above, any other embodiment of the sensor according to the invention than those shown in FIGS. 7 and 8 may be comprised in a field-effect transistor.

FIG. 7 is a schematic cross-sectional view of the basic structure of a field-effect transistor comprising the basic structure of the first embodiment of the sensor according to the invention. The transistor is made of, for example, a silicon semiconductor 12 of p-type and has two silicon layers 13 of n-type integrated therein. The insulator layer 3 is in contact with the semiconductor layers 12, 13. The transistor comprises further a source electrode 14, a drain electrode 15 and a channel 16. The catalytic metal layer 1 constitutes the gate. When a transistor having the basic structure shown in FIG. 7 is utilized for detection of hydrogen gas in a gas sample, hydrogen atoms may be adsorbed at the complete hydrogen atom adsorption surface portion 8, but only those hydrogen atoms adsorbed at the part of the hydrogen atom adsorption surface portion 8 essentially above the channel 16 will influence the voltage shift in the characteristics of the sensor. This should be apparent for a person skilled in the art and is not further explained herein. The term "above" in the term "the part of the hydrogen atom adsorption surface portion essentially above the channel" is utilized to indicate the position of a part of the hydrogen atom adsorption surface portion 8 when the basic structure of the transistor has the orientation shown in FIG. 7.

FIG. 8 is a schematic cross-sectional view of the basic structure of a field-effect transistor comprising the basic structure of the fourth embodiment of the sensor according to the invention. The basic structure shown in FIG. 8 differs from the basic structure shown in FIG. 7 in that the inner surface 7 further comprises a hydrogen atom adsorption inhibited surface portion 9. A hydrogen atom adsorption inhibiting material layer 11 is sandwiched between the hydrogen atom adsorption inhibited surface portion 9 and the insulator layer 3. The main part of the surface portion of the inner surface 7 essentially above the two silicon layers 13 is comprised in the hydrogen atom adsorption inhibited surface portion 9. The surface portion of the inner surface 7 essentially above the channel 16 is comprised in the hydrogen atom adsorption surface portion 8. Thereby, hydrogen atoms are substantially inhibited from being adsorbed at the main part of the surface portion of the inner surface 7 essentially above the two silicon layers 13, but may be adsorbed at the surface portion of the inner surface 7 essentially above the channel 16. Thus, hydrogen atoms may essentially only be adsorbed at the surface portion of the inner surface 7 essentially above the channel 16, where adsorbed hydrogen atoms may influence the voltage shift in the characteristics of the sensor. Furthermore, essentially no hydrogen atoms may be adsorbed at the main part of the surface portion of the inner surface 7 essentially above the two silicon layers 13, where any adsorbed hydrogen atoms may not influence the voltage shift in the characteristics of the sensor. Thereby, essentially no hydrogen atoms are "wasted" on surface parts of the inner surface 7 where they may not influence the voltage shift in the characteristics of the sensor. This should be apparent for a person skilled in the art and is not further explained herein. The term "above" is utilized to indicate the position of a part of the inner surface 7 when the basic structure of the transistor has the orientation shown in FIG. 8.

A hydrogen gas sensitive semiconductor sensor may be utilized as a leak detector in systems using hydrogen gas, as a leak detector in systems and methods using hydrogen gas as a tracer gas for testing and/or locating leaks, or as an alarm detector to indicate the presence of hydrogen gas within, for example, industries using hydrogen gas or gas mixtures containing hydrogen gas (such as petrochemical industries, electrochemical industries, gasworks) for the purpose of preventing explosions.

For example, the hydrogen gas sensitive semiconductor sensor according to the invention may be comprised in a probe, i.e. a device arranged to provide contact between the outer surface of the catalytic metal layer of the sensor and the gas sample in which the presence or concentration of hydrogen gas molecules is to be measured. The device may be arranged to either bring the outer surface of the catalytic metal layer of the sensor in contact with the gas sample or to bring the gas sample in contact with the outer surface of the catalytic metal layer of the sensor. For example, the probe may be a sampling unit. A probe for detection of hydrogen gas comprising a hydrogen gas sensitive semiconductor sensor according to the invention is also within the scope of the invention.

Furthermore, a hydrogen gas detection system comprising a probe and a measuring unit, which probe comprises the sensor according to the invention, is also within the scope of the invention. Hydrogen gas molecules is then sensed by the sensor in the probe based on the hydrogen dipole transducer principle and signals from the sensor due to detection of hydrogen gas molecules are measured and interpreted in the measuring unit. The measuring unit is typically termed detector and may be of any suitable type.

Furthermore, a hydrogen gas detection system according to the invention may, in addition to a probe, which comprises the sensor according to the invention, and a measuring unit, also comprise at least one of the devices in the group of: hydrogen gas source, gas controller, gas pressure regulator, fixture for a test object and fixture controller. Such a system may, for example, be used for leak testing and/or leak location based on utilization of hydrogen gas as a tracer gas. The hydrogen gas source is arranged to constitute a source of tracer gas and may be of any suitable type. The gas controller is arranged to administrate the filling of hydrogen gas from the hydrogen gas source into the object to be tested or into an enclosure surrounding the object to be tested, such as a fixture, and may be of any suitable type. The gas pressure regulator is arranged to control the output pressure from the gas source and may be of any suitable type. The fixture for a test object is arranged to connect to a test object for filling and removing of gas as well as to seal any other openings not constituting leak openings and may be of any suitable type. The fixture controller is arranged to manoeuvre the connections and seals of the fixture and may be of any suitable type.

For example, when a system according to the invention comprising a probe, which comprises the sensor according to the invention, a measuring unit, a hydrogen gas source, a gas controller, a gas pressure regulator, a fixture for a test object and a fixture controller, is utilized for leak detection, an object subject to leak testing is connected to the fixture. The fixture controller is utilized to manoeuvre the connections of the fixture. A gas or gas mixture comprising a traceable amount of hydrogen is subsequently brought from the gas source into the test object under test by the gas controller. The gas pressure regulator is utilized to control the output pressure from the gas source. The probe comprising the sensor is subsequently used to analyse the air surrounding the object under test for an increased presence of hydrogen. Any measurable increase in hydrogen concentration is presented by the measuring unit and is evidence of existing leakage in the tested object. In an analogue manner it is also possible to detect leakage by administrating the traceable gas or gas mixture on the outside of the object under test and analysing the air inside the tested object for an increased presence of hydrogen.

Thus, while there have been shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, it is expressly intended that all combinations of those elements which perform substantially the same function in substantially the same way to achieve the same results are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A hydrogen gas sensitive semiconductor sensor, comprising:
   a catalytic metal layer comprising an outer surface and an inner surface, the outer surface being arranged to freely communicate with the ambient atmosphere, the inner surface comprising at least one hydrogen atom adsorption surface portion, a surface area of the outer surface being at least 100% larger than a total surface area of the at least one hydrogen atom adsorption surface portion of said inner surface, the inner surface further comprising at least one hydrogen atom adsorption inhibited surface portion;
   a semiconductor layer;
   an insulator layer arranged between the catalytic metal layer and the semiconductor layer, such that the at least one hydrogen atom adsorption surface portion of the catalytic metal layer is arranged adjacent to said insulator layer; and
   a hydrogen atom adsorption inhibiting material layer sandwiched between each hydrogen atom adsorption inhibited surface portion and the insulator layer, whereby each hydrogen atom adsorption inhibited surface portion is arranged adjacent to a hydrogen atom adsorption inhibiting material layer and whereby a thickness of the hydrogen atom adsorption inhibiting material layer is 0.001-0.3 μm.

2. The hydrogen gas sensitive semiconductor sensor according to claim 1, wherein the surface area of the outer surface is at least 500% larger than the total surface area of the at least one hydrogen atom adsorption surface portion of said inner surface.

3. The hydrogen gas sensitive semiconductor sensor according to claim 2, wherein the surface area of the outer surface is at Least 5000% larger than the total surface area of the at least one hydrogen atom adsorption surface portion of said inner surface.

4. The hydrogen gas sensitive semiconductor sensor according to claim 1, wherein an upper surface of the catalytic metal layer is assigned a surface-enlarging structure.

5. The hydrogen gas sensitive semiconductor sensor according to claim 4, wherein the inner surface comprises one hydrogen atom adsorption surface portion.

6. The hydrogen gas sensitive semiconductor sensor according to claim 1, wherein the sensor comprises at least two hydrogen atom adsorption inhibiting material layers and wherein all of the hydrogen atom adsorption inhibiting material layers comprise similar hydrogen atom adsorption inhibiting material.

7. The hydrogen gas sensitive semiconductor sensor according to claim 1, wherein the sensor comprises at least two hydrogen atom adsorption inhibiting material layers and wherein at least two of the hydrogen atom adsorption inhibiting material layers comprise different hydrogen atom adsorption inhibiting materials.

8. The hydrogen gas sensitive semiconductor sensor according to claim 1, wherein the hydrogen atom adsorption inhibiting material comprises a non-catalytic metal or a non-catalytic alloy.

9. The hydrogen gas sensitive semiconductor sensor according to claim 8, wherein the hydrogen atom adsorption inhibiting material comprises aluminum, an aluminum alloy or chromium.

10. The hydrogen gas sensitive semiconductor sensor according to claim 1, wherein the sensor is a metal-insulator-semiconductor field-effect device.

11. The hydrogen gas sensitive semiconductor sensor according to claim 1, wherein the sensor is a Schottky-barrier device.

12. The hydrogen gas sensitive semiconductor sensor according to claim 1, wherein the sensor detects a presence of hydrogen gas molecules in a gas sample.

13. The hydrogen gas sensitive semiconductor sensor according to claim 1, wherein the sensor measures a concentration of hydrogen gas molecules in a gas sample.

14. A probe for detection of hydrogen gas, comprising:
a hydrogen gas sensitive semiconductor sensor comprising:
a catalytic metal layer comprising an outer surface and an inner surface, the outer surface being arranged to freely communicate with the ambient atmosphere, the inner surface comprising at least one hydrogen atom adsorption surface portion, a surface area of the outer surface being at least 100% larger than a total surface area of the at least one hydrogen atom adsorption surface portion of said inner surface, the inner surface further comprising at least one hydrogen atom adsorption inhibited surface portion;
a semiconductor layer;
an insulator layer arranged between the catalytic metal layer and the semiconductor layer, such that the at least one hydrogen atom adsorption surface portion of the catalytic metal layer is arranged adjacent to said insulator layer; and
a hydrogen atom adsorption inhibiting material layer sandwiched between each hydrogen atom adsorption inhibited surface portion and the insulator layer, whereby each hydrogen atom adsorption inhibited surface portion is arranged adjacent to a hydrogen atom adsorption inhibiting material layer and whereby a thickness of the hydrogen atom adsorption inhibiting material layer is 0.001-0.3 μm.

15. A hydrogen gas detection system, comprising:
a probe comprising a hydrogen gas sensitive semiconductor sensor comprising
a catalytic metal layer comprising an outer surface and an inner surface, the outer surface being arranged to freely communicate with the ambient atmosphere, the inner surface comprising at least one hydrogen atom adsorption surface portion, a surface area of the outer surface being at least 100% larger than a total surface area of the at least one hydrogen atom adsorption surface portion of said inner surface, the inner surface further comprising at least one hydrogen atom adsorption inhibited surface portion;
a semiconductor layer;
an insulator layer arranged between the catalytic metal layer and the semiconductor layer, such that the at least one hydrogen atom adsorption surface portion of the catalytic metal layer is arranged adjacent to said insulator layer; and
a hydrogen atom adsorption inhibiting material layer sandwiched between each hydrogen atom adsorption inhibited surface portion and the insulator layer, whereby each hydrogen atom adsorption inhibited surface portion is arranged adjacent to a hydrogen atom adsorption inhibiting material layer and whereby a thickness of the hydrogen atom adsorption inhibiting material layer is 0.001-0.3 μm; and
a measuring unit.

16. The hydrogen gas detection system according to claim 15, further comprising:
a hydrogen gas source.

17. The hydrogen gas detection system according to claim 15, further comprising:
a gas controller.

18. The hydrogen gas detection system according to claim 15, further comprising:
a fixture for a test object.

19. The hydrogen gas detection system according to claim 15, further comprising:
a gas pressure regulator.

20. The hydrogen gas detection system according to claim 15, further comprising:
a fixture controller.

* * * * *

UNITED STATES PATENT AND TRADEMARK OFFICE
CERTIFICATE OF CORRECTION

PATENT NO. : 7,622,080 B2  
APPLICATION NO. : 11/524332  
DATED : November 24, 2009  
INVENTOR(S) : Fredrik Enquist It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 161 days.

Signed and Sealed this

Twenty-sixth Day of October, 2010

David J. Kappos  
*Director of the United States Patent and Trademark Office*